United States Patent
Bichler et al.

(10) Patent No.: US 12,281,686 B2
(45) Date of Patent: Apr. 22, 2025

(54) DEVICE FOR STABILIZING MOVEMENTS OF TWO PARTS OF A BODY REGION AND/OR OF A SPORTS DEVICE

(71) Applicant: BETTERGUARDS TECHNOLOGY GmbH, Berlin (DE)

(72) Inventors: Vinzenz Bichler, Berlin (DE); Timo Stumper, Berlin (DE); Oscar Buschinger, Berlin (DE)

(73) Assignee: BETTERGUARDS TECHNOLOGY GmbH, Berlin (DE)

(*) Notice: Subject to any disclaimer, the term of this patent is extended or adjusted under 35 U.S.C. 154(b) by 116 days.

(21) Appl. No.: 17/777,167

(22) PCT Filed: Nov. 16, 2020

(86) PCT No.: PCT/EP2020/082268
§ 371 (c)(1),
(2) Date: May 16, 2022

(87) PCT Pub. No.: WO2021/094611
PCT Pub. Date: May 20, 2021

(65) Prior Publication Data
US 2022/0403905 A1  Dec. 22, 2022

(30) Foreign Application Priority Data
Nov. 15, 2019 (DE) ..................... 10 2019 130 999.9

(51) Int. Cl.
*F16F 9/32* (2006.01)
*A61F 5/01* (2006.01)
(Continued)

(52) U.S. Cl.
CPC .......... *F16F 9/3214* (2013.01); *A61F 5/0102* (2013.01); *F16F 9/19* (2013.01);
(Continued)

(58) Field of Classification Search
CPC ............. F16F 9/3214; F16F 9/516; F16F 9/19
See application file for complete search history.

(56) References Cited

U.S. PATENT DOCUMENTS 3,992,493 A * 11/1976 Whyte ................... B65D 85/73
261/DIG. 7
5,190,126 A * 3/1993 Curnutt .................. F16F 9/466
188/269

(Continued)

FOREIGN PATENT DOCUMENTS

| EP | 1437524 B1 | 7/2006 |
| EP | 2842527 A1 | 3/2015 |
| EP | 3092980 A1 | 11/2016 |

OTHER PUBLICATIONS

International Search Report for corresponding International (PCT) application No. PCT/EP2020/082268; 6 pages, dated Feb. 9, 2021.

*Primary Examiner* — Abiy Teka
(74) *Attorney, Agent, or Firm* — Ruggiero McAllister & McMahon LLC

(57) ABSTRACT

An apparatus for stabilizing movements of two parts of a body region and/or of a sports device which are movable relative to one another, comprising a receptacle, which can be fixed to a first part of the region and/or device. An active body arrangement with an active body is received movably in the receptacle and can interact with the filling medium. A force transmission body can be fixed to a second part of the same region and/or device for transmitting an external force to the active body. The active body comprises at least one through-opening through which a filling medium in the receptacle can flow. The active body arrangement has a sealing lip for sealing a gap between an inner side of the receptacle and a lateral region of an outer side of the active body arrangement, the sealing lip being arranged on an outer side of the active body.

14 Claims, 9 Drawing Sheets

(51) Int. Cl.
*F16F 9/19* (2006.01)
*F16F 9/516* (2006.01)
*F16F 9/58* (2006.01)

(52) U.S. Cl.
CPC .............. *F16F 9/516* (2013.01); *F16F 9/585* (2013.01); *A61F 2005/0169* (2013.01); *F16F 2224/041* (2013.01)

(56) References Cited

U.S. PATENT DOCUMENTS

| | | |
|---|---|---|
| 5,712,011 A | 1/1998 | McMahon et al. |
| 5,730,263 A | 3/1998 | Grundei et al. |
| 10,098,775 B2 | 10/2018 | Bichler et al. |
| 2014/0015176 A1 | 1/2014 | Wetzel et al. |
| 2016/0213549 A1 | 7/2016 | Fumiya et al. |
| 2017/0304057 A1 | 10/2017 | Bichler et al. |
| 2018/0223941 A1* | 8/2018 | Grzesik .................. F16F 9/483 |

* cited by examiner

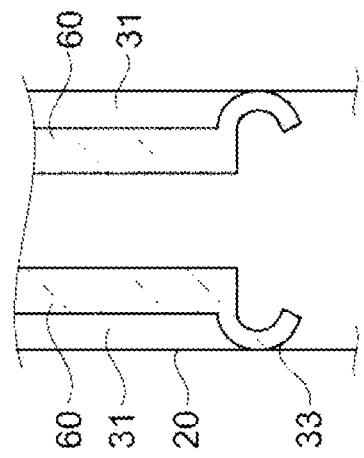
Fig. 4c
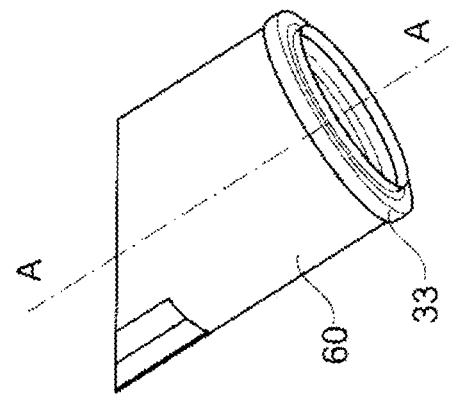
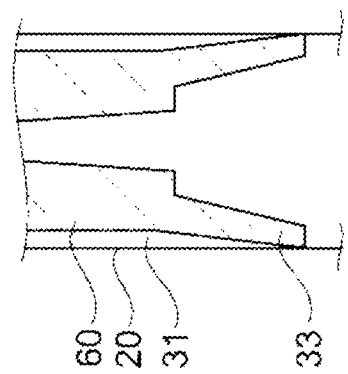
Fig. 4b
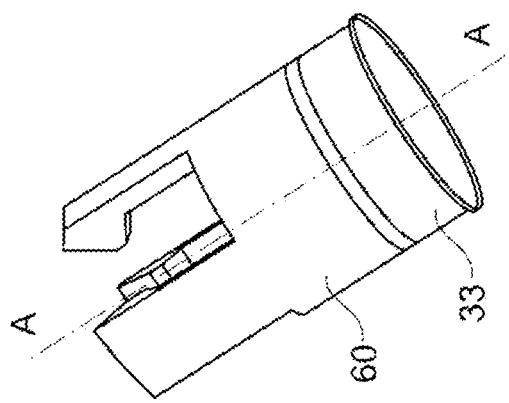
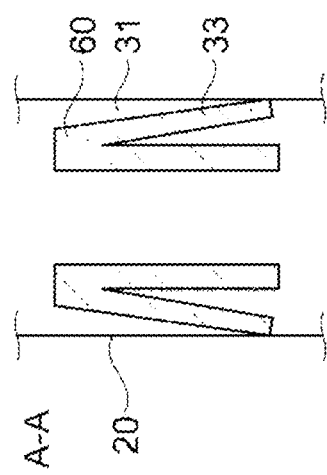
Fig. 4a
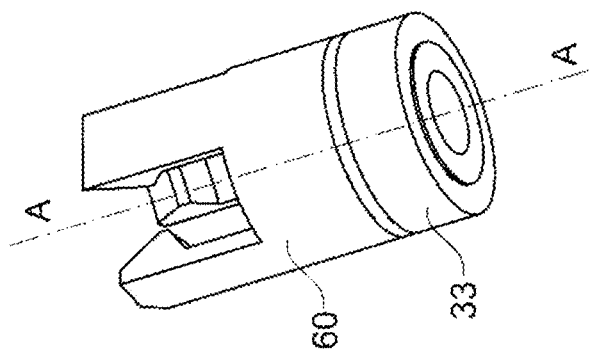

DEVICE FOR STABILIZING MOVEMENTS OF TWO PARTS OF A BODY REGION AND/OR OF A SPORTS DEVICE

TECHNICAL FIELD

The present disclosure relates to a device for stabilizing movements of two parts, movable relative to one another, of a body region and/or a sports device.

DESCRIPTION OF THE RELATED TECHNOLOGY

It is known for body joints, muscles and tendons to be stabilized by means of devices which make an adaptive movement limitation possible. It is also known for sports devices that can be subjected to jerky movements to be provided with adaptive movement limitation devices.

Inter alia, the adaptive behavior of devices of this type is achieved by virtue of the fact that two bodies move relative to one another, a filling medium being situated between the bodies. Here, one body of the device can form a receptacle which is filled with the filling medium. The other body can form a pull-out body which is arranged movably in the receptacle. The filling medium can flow in the region between the receptacle and the pull-out body when the two bodies move relative to one another. The flowing speed of the filling medium depends decisively on the cross-sectional area perpendicularly with respect to a relative displacement direction of the receptacle and the pull-out body. This cross-sectional area which is available for the flow for the filling medium is also called a hydraulic diameter and is ultimately decisive for the reactive behavior of the device in the case of an external action of force.

The resistance, with which the device counters external forces, can thus be specified by way of the selection of the hydraulic diameter. The devices can be fixed between two body locations of a user or two elements of a sports device which can move relative to one another.

If physiological forces or physiological speeds (that is to say, forces which are not critical for the body part or component to be stabilized correspondingly) are introduced into the device via the two body locations of the user, a corresponding relative movement of the receptacle and the pull-out body and therefore a movement of the body part to be stabilized is permitted in accordance with the hydraulic diameter in the device.

If, in contrast, non-physiological forces (that is to say, forces which are critical for the body part or component to be stabilized correspondingly) are introduced into the device, a relative movement between the pull-out body and the receptacle is possible only with a very high effort on account of the change in the hydraulic diameter. The device blocks.

A device of this type is known, for example, from the U.S. Pat. No. 5,712,011. U.S. Pat. No. 5,712,011 discloses a device with two bodies which are movable relative to one another. A first body comprises a receptacle which is filled with a fluid. The second body extends at least partially into the receptacle of the first body and is configured to enter into an interaction with the fluid. Relative movements between the first and the second body can be damped by way of the interaction.

In the blocked state, very high pressure loads can arise in the device, which pressure loads can damage the device. An excessively hard or brittle material selection of the receptacle has the disadvantage that, although the receptacle withstands the pressure loads, it impairs the wearing comfort of the devices on body parts and joints. On the other hand, an excessively elastic material selection of the receptacle has the consequence that the receptacle bends outward at high pressures, or bulges as it were, and the filling medium can escape out of a space which is compressed in the blocked state along the inner wall of the receptacle past the seal and/or the active body and a sealing ring which is attached thereto. As a result, the device no longer blocks as desired, and the operating principle of the device is impaired.

It has been shown that O-rings cannot adapt to the changed diameters of the receptacle which are to be attributed to the bending of the receptacle at a corresponding pressure. Furthermore, it has been shown that O-rings cannot always maintain their position in the receptacle on account of the high pressure loads. As a result of the escape of the filling medium past the seal, the O-ring is displaced and even slips over the active body and impairs the functional capability of the device up to a total failure, that is to say the device switches too early or too late or not at all anymore, that is to say no longer permits a reproducibility of the operating principle of the device.

Furthermore, the devices which are known in the prior art have the disadvantage that they do not block in the range of the physiological speeds and there is the risk that an active body impacts on the receptacle in the case of a continuing movement at speeds of this type, as a result of which the device can be damaged.

SUMMARY OF THE DISCLOSURE

A device for stabilizing of movements of two parts, movable relative to one another, of a body region and/or a sports device is disclosed.

A device is specified for stabilizing movements of two parts, movable relative to one another, of a body region, in particular two body joints movable relative to one another, and/or a sports device, comprising a receptacle which can be fixed on a first part of a body region and/or a sports device, the receptacle being filled with a filling medium, and at least one active body arrangement which is received displaceably in the receptacle and can interact with the filling medium, a force transmission body which can be fixed on a second part of the same body region and/or the same sports device for transmitting an external force or speed to the active body, the active body comprising at least one passage opening, through which filling medium can flow. According to the disclosure, the active body arrangement has a sealing lip for sealing a gap between an inner side of the receptacle and a lateral region of an outer side of the active body arrangement, the sealing lip being arranged on an outer side of the active body.

For example, the sealing lip is arranged on an outer side of the active body in the circumferential direction and/or upper side and/or lower side of the active body.

In the interior of the receptacle of the device, high pressure loads can arise on the active body as a result of the critical displacement speeds and the resulting forces in the blocked state of the device. Depending on the diameter of the receptacle, pressure loads of different magnitude can arise. It is the case that the lower the diameter, the higher the maximum pressure loads which occur. For example, pressure loads of from 160 to 280 bar can arise.

Pressure loads of this type can be kept under control by way of a corresponding design of the receptacle, that is to say reinforcement of the wall thickness. This is not desirable, however, since it in turn entails losses in the wearing comfort of the device on the body joints or regions on account of a large construction of this type which unnecessarily increases the space requirement of the device in sports devices. It is to be noted, furthermore, that a pressure load is more difficult to keep under control, the smaller the diameter of the receptacle is, which in turn means that the wall thickness would have to be reinforced even further. Therefore, the reinforcement of the wall thickness is not a suitable solution for the application-specific purpose of the device, since the latter is to be as small as possible for use in sports devices or on body regions. In the present case, the term "sports devices" also comprises sports apparel such as, for example, sports bras, socks, shoes, gloves.

In order not to impair the wearing comfort and/or not to further increase the wall thickness, the receptacle is to be configured in such a way that it is not too hard/brittle (for example, a modulus of elasticity in the range from 1500 to 1800 MPa, test method DIN EN ISO 6721-1 (2018 March)). The receptacle can be made from a plastic which has sufficiently elastic properties.

It has been shown that a material selection with elastic properties is particularly suitable for the receptacle. When subjected to high pressure loads, the walls of the receptacle bend outward, what is known as bulging. The receptacle is deformed slightly within the permissible stress. Bursting of the receptacle is avoided as a result of the elastic properties of the receptacle. A configuration of this type of the receptacle is also advantageous because the elastic properties of the receptacle do not abruptly stop the incorrect joint movement in the blocked state of the device, but rather cushion it moderately. As a result of this cushioning effect, an intake or absorption of energy can occur, as a result of which the surrounding body structures/components are loaded to a lesser extent.

As a result of the bulging, however, the cross section or the diameter, respectively, of the receptacle is increased partially, which, owing to a lack of an adequate seal, has the consequence of a flow through the gap with filling medium and can lead to a pressure loss in the interior of the receptacle. As a result of the pressure loss which occurs as a consequence of the bulging, a considerably lower counterforce is generated by the active body, which leads to the device no longer blocking, and it not being possible for a sufficient protective action of the device to be provided and/or maintained. The active body can possibly even slip, and impact on the upper end of the receptacle, which can lead to damage of the active body and the receptacle.

This problem can be solved by way of the sealing lip. The sealing lip makes it possible to design the receptacle of the device to be elastic (for example, a modulus of elasticity in the range from 300 to 700 MPa, test method DIN EN ISO 6721-1 (2018 March)) in such a way that, although the receptacle bulges under high pressure loads, the filling medium cannot escape or only escapes to a small extent through the gap, since the sealing lip adjusts itself to the changes in the diameter of the receptacle.

The receptacle can be produced from metal. As an alternative, the receptacle can be produced from plastic.

A configuration of the receptacle from plastic makes it possible to provide the receptacle with elastic properties. This can take place, for example, by means of an injection molding method. In one example, the receptacle can be produced in one piece with other parts, for example a restoring element, in particular a sealing hose, which is responsible for restoring the active body into the starting state. The advantage here is that the manufacturing costs can be reduced many times over, since fewer parts have to be assembled.

A further advantage of the sealing lip consists in that tolerances in the gap size which can occur as a result of draft angles in the case of the injection molding method are compensated for by way of the sealing lip. Tolerances or variances in the gap size likewise lead to the blocking action of the device not always occurring in constant force and/or speed ranges. The adjusting function of the sealing lip to the gap tolerances/variances therefore ensures an improved reproducibility of the operating principle of the device. The seal therefore always adapts to a changed diameter in the receptacle, and ensures uniform switching of the device, that is to say uniform blocking of the device in the case of the introduction of tensile forces on the force transmission body above a predefined tensile force and/or speed.

The circumferential sealing lip therefore affords the advantage that it compensates for a varying gap or spacing between the active body and an inner wall of the receptacle, that is to say that it is also deformed in the case of curving or bulging of the receptacle and can therefore maintain the pressure in the receptacle when the device blocks.

Pressing in of the receptacle in terms of the diameter to form a slightly oval cross section can also be compensated for by way of the elasticity of the sealing lip. The receptacle becomes oval as a result of being pressed in. The sealing lip is elastic in such a way that different gap sizes along the circumference can be compensated for. The sealing lip is therefore compressed at certain points along the circumference and is expanded at other locations, in order to compensate for an increase in the gap. As a result of an adaptive behavior of said a sealing lip, the receptacle can be of more elastic configuration. As a result, the wearing comfort of the device can be improved.

Furthermore, the sealing lip can be used in a receptacle with an oval cross section. The sealing lip is elastic in such a way that different gap sizes along the circumference of the active body can be compensated for. The sealing lip can therefore be compressed at certain points along the circumference and can be expanded at other locations, in order to compensate for different gap sizes on account of the oval cross section.

The filling medium can be a Newtonian fluid such as, for example, oil, in particular silicone oil. A dilatant fluid can also be used as an alternative.

The active body and the filling medium are in an operative connection with one another in such a way that, in the case of a force or speed acting on the active body below a predefined threshold value, the active body can displace the filling medium through the passage opening, that is to say the filling medium can flow relative to the active body within the receptacle. In the case of a force or speed acting on the active body which is greater than or equal to the predetermined threshold value, the active body acts on the filling medium in such a way that a flow of the filling medium relative to the active body through the passage opening is not possible or is merely partially possible.

The sealing lip can also be called a sealing diaphragm.

In accordance with one embodiment, the active body arrangement has a region of the sealing lip, which region bears against the inner side of the receptacle and extends at an angle ($\alpha$, $\beta$) with respect to a lateral region of the outer side of the active body, the angle ($\alpha$, $\beta$) being variable, in order for it to be possible for size fluctuations of the gap between the inner side of the receptacle and the lateral region of the outer side of the active body arrangement to be compensated for and in order to seal the gap even in the case of size fluctuations of this type.

In the present case, a size fluctuation is to be understood to mean a change in the spacing between the inner side of the receptacle and the lateral region of the outer side of the active body.

The spacing changes, in particular, by virtue of the fact that the inner diameter of the receptacle changes in sections as a result of the bulging.

In accordance with one embodiment, it is possible for the variable angle ($\alpha$, $\beta$) to compensate for a size fluctuation of the gap of up to 15%, in relation to the original size of the gap.

An adaptive sealing lip of this type has the advantage that the receptacle can be of elastic configuration without impairing the functional capability of the device. Furthermore, the receptacle can be of thin-walled configuration. This is particularly advantageous, since the device can accordingly be of small dimensions, as a result of which it is particularly suitable for use in the sporting area.

For example, the sealing lip for a receptacle with a diameter of 8 mm can compensate for a partial change in the diameter on account of the bulging of up to 1 mm, for example 1.2 mm. Structurally planned bulging of this type of the receptacle additionally has the advantage that the device also absorbs the incorrect joint movement in the blocked state.

Furthermore, the sealing lip is configured in such a way that it can be restored again after the deformation, with the result that it is reset or springs back (largely on its own) approximately into the starting state again after an adaptive deformation. For this purpose, the sealing lip should have corresponding moduli of elasticity as described above.

The passage opening fluidically connects a first chamber to a second chamber in the interior space of the receptacle.

The receptacle has a greater diameter than the active body. The gap is formed by way of the different diameters of the active body and the receptacle.

In accordance with one embodiment, it is possible for the filling medium to flow through the gap above a size of the gap which is increased by more than 15%, in relation to the original size of the gap, in order to avoid a critical internal pressure in the receptacle.

The bulging is therefore intentionally compensated for only up to a certain degree, that is to say until a certain (critical) internal pressure arises in the receptacle. At a critical internal pressure, the receptacle bulges to such an extent that the sealing lip seals the gap only partially, in order to counteract a critical internal pressure arising. In the example depicted above, the diameter would increase, for example, by more than 1 mm or 1.2 mm.

In accordance with one embodiment, the sealing lip and the active body are formed in one piece. The sealing lip and the active body together form the single-piece active body arrangement. As a result, releasing or slipping of the seal from the active body can be avoided, and the securing of the sealing action of the gap between the receptacle and the active body can be improved. Moreover, the single-piece configuration makes simplified assembly possible, which in turn has a positive effect on the manufacturing costs of the device.

In accordance with one embodiment, the receptacle comprises an opening, the force transmission body running through the opening, and the sealing lip being arranged at an end of the active body, which end faces the opening of the receptacle. The force transmission body can be displaced along a pull-out direction. The pull-out direction runs substantially along the longitudinal axis of the active body. This arrangement of the sealing lip on the active body has the advantage that, in addition to the sealing function, the sealing lip also provides a buffer function against impact of the active body on the receptacle.

The longitudinal axis is to be understood to mean an axis which runs along the pull-out direction or the center line of the force transmission body.

As an alternative, an additional sealing lip can also be arranged at an end of the active body, which end lies opposite the opening. As a result, the sealing effect can be increased further, and impact of the active body on that region of the receptacle which lies opposite the opening can be avoided.

In one example, the sealing lip extends at least partially from the outer circumference of the active body in the direction of an inner wall of the receptacle and can bear against the latter. As a result, contact of the sealing lip can be ensured in a starting position, that is to say in which the receptacle does not bulge. The sealing lip is prestressed, for example, in such a way that the sealing lip bears sealingly against the inner wall of the receptacle in the starting position.

As an alternative, the sealing lip is not prestressed, but is rather configured in such a way that, in the starting position, the sealing lip allows a small gap between the sealing lip and the inner wall of the receptacle. If the device is activated in the range of the non-physiological speeds, the filling medium acts on the sealing lip, with the result that the latter is pressed onto the inner wall of the receptacle.

In accordance with one embodiment, the sealing lip extends at least partially in the direction of the opening of the receptacle beyond the active body, in order to form a projection in a pull-out direction of the active body.

An orientation of this type of the sealing lip has the advantage that the sealing lip is pressed onto the inner wall of the receptacle by way of the filling medium when the force transmission body is pulled out of the device in the pull-out direction. The filling medium is compressed in a first chamber of the receptacle, that is to say the chamber which is closer to the opening of the receptacle, and flows at least along the inner wall of the receptacle in the opposite direction to the pull-out movement of the active body. The filling medium therefore presses on the sealing lip, as a result of which the sealing lip is pressed onto the inner wall of the receptacle and boosts the sealing action of the sealing lip.

Furthermore, an arrangement of this type has the advantage that the sealing lip acts in a buffering manner if the active body impacts with a second end, that is to say the end where the opening of the receptacle is arranged. This is the case, for example, when the device is activated at physiological speeds and/or the active body is pulled onto the stop of the receptacle. Damage of the active body and/or the receptacle as a result of the impact on the receptacle can be avoided by way of the damping action of the sealing lip.

It is possible for the sealing lip to be spread in a parasol-like or leg-like manner by the active body in order to close the gap between the active body arrangement and the receptacle. This can ensure fully circumferential sealing of the gap.

In the present case, parasol-like is to be understood to mean an orientation in space which points away from a longitudinal axis of the active body. The sealing lip which is spread by the active body is arranged in space at an angle $\alpha$, $\beta$ between the longitudinal axis and a perpendicular of the longitudinal axis, that is to say in the angular range of from greater than 0° and less than 90°, for example, greater than 10° and less than 80° in relation to the longitudinal axis of the active body. 0° is to be understood to mean an orientation of the sealing lip which runs parallel to the longitudinal axis of the active body. 90° is to be understood to mean an orientation of the sealing lip which runs perpendicularly with respect to the longitudinal axis of the active body. As an alternative, the sealing lip can also be offset partially along the longitudinal axis of the active body and along the circumference of the active body, that is to say, for example, can be arranged in a flower-like manner on the active body.

Furthermore, the active body can also be of conical design.

The sealing lip which projects from the active body can be configured in various forms. For example, the sealing lip can be of rectilinear or curved configuration. Furthermore, that end of the sealing lip which faces the inner wall of the receptacle can have a greater cross section than the rest of the sealing lip. As a result, the contact area on the inner wall for the sealing action can be increased. A tapered cross section of the sealing lip in the region which bears against the active body is advantageous since, as a result, the sealing lip is more flexible, and can therefore compensate for the changes in the diameter of the receptacle in an adaptive manner.

In accordance with one embodiment, the sealing lip has a modulus of elasticity in the range from 300-700 MPa, for example in the range from 350-450 MPa, such as 420 MPa. As a result, a sealing lip is provided which is suitable to both seal the gap between the active body and the receptacle against the throughflow of filling medium in the starting position and to compensate for the gap size changes on account of the bulging or gap size tolerances.

The sealing lip can be made from a polymer, for example a polymer from the class of polyhalogenolefins, such as polytetrafluoroethylene (PTFE). PTFE is particularly low-friction and has elastic properties which are suitable for compensating for the changes in the diameter of the receptacle as a consequence of bulging.

In accordance with a further embodiment, the sealing lip permits a flow of filling medium through the gap above a certain threshold value of a force or speed which acts on the force transmission body and a resulting certain pressure in the receptacle, for example in a first chamber in the receptacle, in order to avoid a critical internal pressure in the receptacle.

For example, slots or flaps are made in the sealing lip which are expanded above a certain threshold value of a tensile force which is exerted on the force transmission body, and the filling medium is allowed to pass through the sealing lip. Below the certain threshold value, the slots and flaps are closed by way of the internal stress of the sealing lip. As a result, the sealing lip acts as a pressure relief valve. This has the advantage that no overpressure arises in the receptacle. In one example, the sealing lip can be configured to ensure, for example, a counterforce of 800 N, regardless of the force, with which the force transmission body is activated. If the force transmission body is activated, for example, with a tensile force of 2000 N, the sealing lip acts as a pressure relief valve by a certain quantity of filling medium being let through the gap via the sealing lip which is permeable above a certain threshold value, in order to always provide a counterforce of, for example, 800 N. As a result, the service life and the safety of the receptacle, for example avoidance of bursting of the receptacle, can be improved.

In one example, the active body can have a stop which limits the movement in the direction of the inner side of the receptacle in a manner which is dependent on a certain pressure. As a result, the sealing lip does not bear against the inner side of the receptacle above a certain pressure, with the result that a small flow of filling medium can pass through the gap, in order to avoid the build-up of an overpressure.

Furthermore, soft braking of the incorrect joint movement can be ensured as a result. This is more favorable in physiological terms than a complete, abrupt stop of the device.

In accordance with a further refinement, an end stop is arranged on the receptacle around an opening of the receptacle, in order to avoid direct impact of the active body on the receptacle.

The end stop is, for example, an elastic, soft plastic which is arranged as a buffer element or cushion on the inner side of the receptacle around the opening of the receptacle. The end stop can also be integrated into the receptacle using the two-component injection molding method.

In a further example, the sealing lip and the end stop can in combination provide a buffering function. This is particularly important when the device does not block, that is to say the movements are in the physiological range. The active body can then pass as far as the stop of the receptacle. Without a buffer, there is the risk that parts of the device, in particular the active body or the sealing lip and the receptacle, are damaged as a result of the impact of the active body on the receptacle. Furthermore, the sealing lip can also be attached to an end which lies opposite the opening of the receptacle, in order to form an impact damping element or a buffer element there.

In accordance with a further embodiment, the active body comprises a first active body and a second active body, the first active body and the second active body being arranged displaceably in the receptacle and it being possible for them to interact with the filling medium, wherein the force transmission body transmits the external force to the first active body, wherein the second active body is coupled elastically to the first active body via a coupling element, wherein the second active body and/or the first active body have at least one passage opening, through which the filling medium can flow, wherein the first active body forms a valve body and the second active body forms a valve seat, wherein the sealing lip is arranged on the second active body.

As a result, a flow of the medium through the passage opening can be permitted or prevented in a manner which is dependent on the valve position. The second active body is arranged closer to the second end of the receptacle in relation to the longitudinal axis of the receptacle, the first active body being arranged closer to the first end in relation to the longitudinal axis.

In one development, the second active body comprises at least one receiving space in the relative displacement direction, the receiving space overlapping with the first active body in relation to the relative displacement direction independently of a relative displacement of the first active body and the second active body with respect to one another.

As a result, it is possible for contact to be provided at all times, that is to say guidance of the first active body on the second active body. As a consequence, there is an overlap of the receiving space of the second body with the first body both when the device is situated in a starting position, in which no external force acts on the device and, in particular, the first and the second active body, and in a blocking position, in which the first active body is seated on the second active body and thereby closes the passage opening.

An overlap of the first active body and the second active body in a relative displacement direction makes it possible for the two active bodies to be guided when they are moved relative to one another on account of an external action of force. As a result, the probability can be increased that the passage opening is closed completely by way of contact of the two active bodies which results in blocking of the passage opening. This contributes to a homogeneous behavior of the device.

The relative displacement direction denotes the direction, in which the first active body and the second active body can be moved relative to one another by way of an external action of force and/or the force transmission body.

In one example, the receptacle has a diameter in the range from 4-15 mm. The selection of the diameter depends on the application. For example, in sports devices, devices with a diameter of 15 mm are used. In the use areas such as in the garment industry, for example shoes, devices with a diameter of 4 mm are used, for example. Devices with small diameters of this type can be used, for example, for weaving or knitting into textiles. The smaller the diameter of the receptacle, the better the wearing comfort of the device on the body and/or the smaller the space requirement of the device if attached to sports devices.

The sealing lip makes it possible for the device to have correspondingly small dimensions, as a result of which it is particularly suitable for use in the sporting area. As an alternative, the devices can also be used for occupational safety, in the military field or generally for fall prevention.

The receptacle can have a wall thickness between the 1 and 3 mm, for example in the range between 1.5 and 2.5 mm, such as 2 mm.

In accordance with a further refinement, a gap size between the first active body and the receptacle is different than a gap size between the second body and the receptacle.

In accordance with one embodiment, the sealing lip is molded onto the active body by way of a two-component injection molding production method, at least the sealing lip comprising a polymer, in particular from the class of polyhalogenolefins, for example polytetrafluoroethylene (PTFE). PTFE is particularly low-friction and has elastic properties which are suitable for compensating for the changes in the diameter of the receptacle. Furthermore, PTFE has a high reproducibility in the production process. As an alternative, the active body can be designed or molded from a component in such a way that the active body forms the sealing lip per se and curves, or does not take shape, in an adaptive manner depending on the force and speed which act.

In one development, the receptacle is a hollow fiber. This is advantageous, for example, in the case of the integration of the device into textile products such as, for example, bandages, pads, gloves, shoes, socks and the like. The operating principle, on which the device is based, makes a particularly small overall design possible. Integrated into a hollow fiber, a device for movement restriction is thus possible which is suitable, in particular, for the sporting area.

The device for stabilizing body joints and/or sports devices makes a configuration of the receptacle with elastic properties possible. Bulging of the receptacle in the case of high pressure loads of the device and an associated pressure loss are compensated for by way of the sealing lip, since the latter adjusts to the changed cross section of the receptacle in the case of bulging.

BRIEF DESCRIPTION OF THE FIGURES

Further embodiments and aspects of the present disclosure are explained in greater detail by way of the following description of the figures, in which.

DETAILED DESCRIPTION OF EXEMPLARY EMBODIMENTS

Figure 1C:
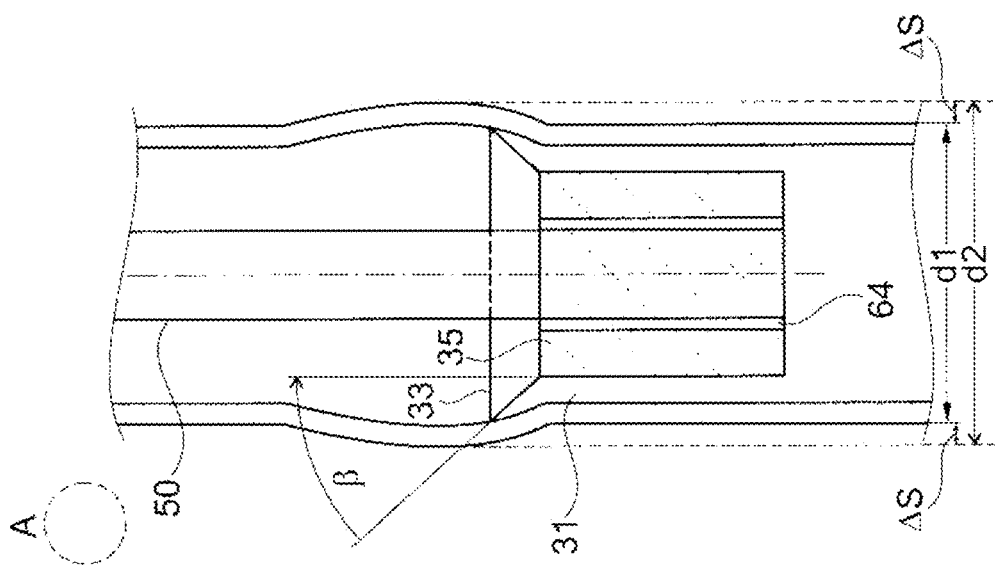
FIG. 1a schematically shows a sectional view of a device for stabilizing movements of two parts, movable relative to one another, of a body region and/or a sports device in accordance with one embodiment, FIG. 1b schematically shows a detailed view of the sectional view of the device from FIG. 1a in the non-blocked state of the device, FIG. 1c schematically shows a detailed view of the sectional view of the device from FIG. 1a in the blocked state, FIG. 1d schematically shows a perspective view of the device from FIG. 1a, FIG. 2 schematically shows a sectional view of a device for stabilizing movements of two parts, movable relative to one another, of a body region and/or a sports device in accordance with a further embodiment.

In the following, exemplary embodiments will be described on the basis of the figures. Here, identical, similar or identically acting elements are denoted by way of identical reference signs. In order to avoid redundancies, a repeated description of these elements is dispensed with in part in the following description.

In the following text, a device 1 for stabilizing movements of two parts, movable relative to one another, of a body region and/or a sports device will be described on the basis of FIGS. 1a to 1c. The device comprises a receptacle 20 which can be fixed on a first part of a body region and/or a sports device, the receptacle 20 being filled with a filling medium 30, and at least one active body arrangement with an active body which is received displaceably in the receptacle 20 and can interact with the filling medium, a force transmission body 50 which can be fixed on a second part of the same body region and/or the same sports device for transmitting an external force to the active body 35, the active body 35 comprising at least one passage opening 64, through which filling medium can flow. The active body arrangement has a sealing lip 33 for sealing a gap 31 between an inner side of the receptacle 20 and a lateral region of an outer side of the active body arrangement 35, the sealing lip 33 being arranged on an outer side of the active body 35.

The active body 35 divides the interior space 25 of the receptacle 20 into a first chamber 23 and a second chamber 24. The force transmission body 50 is fastened to the active body 35 which runs longitudinally through the second chamber 24 and exits from the receptacle 20 at a second end 22 thereof. The free end (shown in FIG. 1a) of the force transmission body 50 can be connected to a body part of a user (not shown) by means of corresponding attachment elements, or can be connected to a sports device, in order to transmit a tensile force which emanates from the body part or the sports device via the force transmission body 50 to the active body 35. The receptacle 20 comprises a first attachment element for the transmission of force between the receptacle 20 and the first body (not shown), and the force transmission body 50 comprises a second attachment element for the transmission of force between the force transmission body 50 and the second body (not shown). The first attachment element is arranged in the region of the receptacle opening for the transmission of force between the receptacle 20 and the first body (not shown). In one example, the first attachment element is configured as a flange.

The first attachment element serves as an interface for the transmission of force between the first non-device body and the device 1. The second attachment element is arranged on the exposed part of the force transmission body 50, which second attachment element serves as an interface for the transmission of force between a second non-device body and the device 1. This therefore results, in the case of loading, in a force flow between the first attachment element, the filling medium 30, the force transmission body 50 and the second attachment element.

The receptacle 20 is closed by way of a closure 26 in the region of a first end 21 (see FIG. 2), with the result that filling medium which is situated in the receptacle 20 can be retained.

A sealing body 29 is arranged in the region of the second end 22 (see FIG. 2) of the receptacle 20, which sealing body 29 seals the interior space of the receptacle 20 with respect to the force transmission body 50. Here, the receptacle 20 has an opening 52, through which the force transmission body 50 exits from the interior space of the receptacle 20.

The active body 35 can be moved by means of the force transmission body 50 through the filling medium in the direction of the second end 22. Here, the receptacle 20 is connected to a first body or sports device location, and the force transmission body 50 is connected to a second body or device location, it being possible for the first body or device location and the second body or device location to move relative to one another.

The device 1 can be dimensioned in an application-specific manner, with the result that the device 1 permits physiological movements of the user. If the active body 35 is moved within the context of a physiological movement by means of the force transmission body 50 in the direction of the second end, filling medium can flow, as shown here, through the passage opening 64 between the receptacle 20 and the active body 35 or through a valve which is arranged in the active body 35 (see FIG. 2) from the second chamber 24 into the first chamber 23. The flow speed of the filling medium depends decisively on the cross-sectional area perpendicularly with respect to a pull-out direction B of the receptacle 20 and the active body 35. This cross-sectional area which is provided for flow for the filling medium is also called a hydraulic diameter and is ultimately decisive for the reactive behavior of the device in the case of an external action of force. The resistance, with which the device 1 counteracts external forces or speeds which act, can thus be specified by way of the selection of the hydraulic diameter. Here, the arrows represent the flow direction S of the filling medium. If a force no longer acts on the active body 35 via the force transmission body 50, the body 35 can be moved back into the starting position again by means of a restoring element 42 (see FIG. 6), wherein the filling medium 30 flows from the first chamber 23 into the second chamber 24.

If, in contrast, non-physiological forces, that is to say forces which are critical for the body part or component which is correspondingly to be stabilized, are introduced into the device, a relative movement between the active body 35 and the receptacle 20 is still possible only with a very high effort on account of the hydraulic diameter. The filling medium 30 belongs to Newtonian fluids, such as silicone oil, for example. As an alternative, dilatant fluids can also be used as filling medium. Moreover, a plastic can also be used.

Figure 1B:
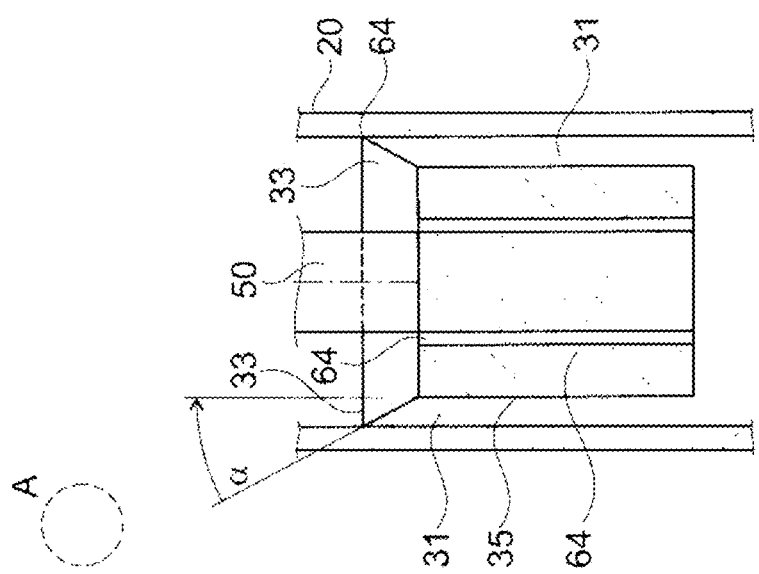
Figure 1A:
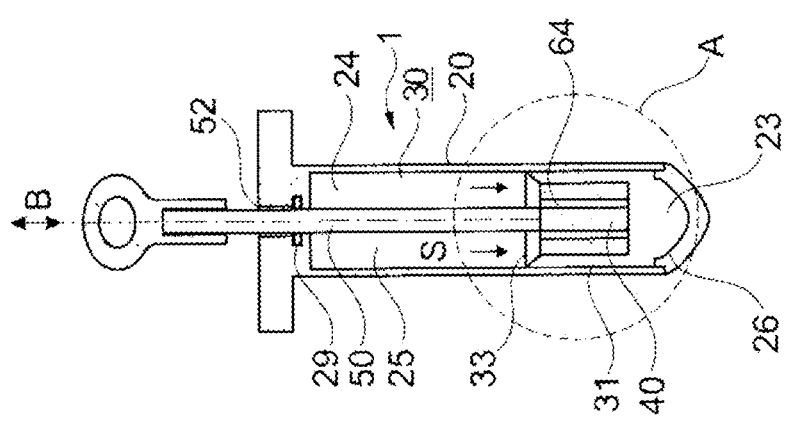

As is shown in FIG. 1*b* and FIG. 1*c* in a detailed excerpt of FIG. 1*a*, the active body arrangement, that is to say the active body 35 and the sealing lip 33, has a region, bearing against the inner side of the receptacle 20, of the sealing lip which extends at an angle ($\alpha$, $\beta$) with respect to a lateral region of the outer side of the active body, the angle ($\alpha$, $\beta$) being variable, in order for it to be possible for size fluctuations ($\Delta S$) of the gap 31 between the inner side of the receptacle 20 and the lateral region of the outer side of the active body arrangement to be compensated for, and in order for the gap 31 to be sealed even in the case of size fluctuations of this type.

FIG. 1*b* shows a detailed excerpt of the device from FIG. 1*a*. It is shown here that the sealing lip 33 bears against the inner wall of the receptacle 20 at an angle $\alpha$ in relation to the longitudinal axis of the active body 35, in order to prevent a flow of the filling medium through the gap 31, that is to say the gap 31 is substantially sealed or bridged by way of the sealing lip 33. The sealing lip 33 and the active body 35 can be formed in one piece, as shown here, and can form the active body arrangement. As a result, the release of the sealing lip 33 from the active body 35 can be avoided. As an alternative, the sealing lip and the active body can also be configured in multiple pieces.

In the embodiment which is shown in FIGS. 1*a* to 1*c*, the sealing lip 33 extends in the direction of the opening 52 of the receptacle 20 beyond the active body 35, in order to form a projection in a pull-out direction of the active body 35. An orientation of this type of the sealing lip 33 has the advantage that the sealing lip 33 is pressed onto the inner wall of the receptacle 20 by way of the filling medium when the force transmission body 50 is pulled out of the device in the pull-out direction B. The filling medium is compressed in the second chamber 24 of the receptacle, and the filling medium flows at least along the inner wall of the receptacle 20 in the opposite direction to the pull-out direction, that is to say toward the active body 35. The filling medium therefore presses onto the sealing lip 33, as a result of which the sealing lip 33 is pressed onto the inner wall of the receptacle 20 and boosts the sealing action of the sealing lip 33.

FIG. 1*c* shows the sealing lip 33 in a state, in which the receptacle 20 curves or bulges on account of a pressure increase in the interior of the receptacle. In the interior of the receptacle of the device, very high pressures of up to 280 bar can arise as a result of the critical displacement speeds and the resulting forces on the active body 35. The receptacle is made from an elastic material which curves or bulges outward in the case of high pressure loading, that is to say the walls of the receptacle curve arcuately outward.

The cross section of the receptacle 20 is increased partially by way of the bulging of the receptacle 20. The sealing lip 33 is, however, elastic in such a way that no filling medium flows through the gap 31, even if the cross section of the receptacle 20, that is to say the diameter of the receptacle, changes. As shown in FIG. 1*c*, the sealing lip widens toward the outside, that is to say in the direction of the inner wall of the receptacle, in order to compensate for the curving. In relation to the longitudinal axis of the active body, the sealing lip then no longer lies at the angle α in space, but rather at the angle β, β being greater than α. As a result, no pressure loss arises in the interior of the receptacle 20, in particular in the second chamber 24, with the result that the function of the device 1 can be preserved.

The circumferential sealing lip therefore has the advantage that it compensates for a varying gap 31 or spacing between the active body 35 and an inner wall of the receptacle 20, that is to say that it also deforms in the case of curving or bulging of the receptacle 20, and therefore can maintain the pressure in the receptacle 20 when the device 1 blocks.

In accordance with one embodiment, the variable angle (α, β) can compensate for a size fluctuation of the gap 31 of up to 15%, in relation to the original size of the gap 31. In other words, the sealing lip 33 is of adaptive design in such a way that the sealing lip 33 can seal even in the case of a changed diameter d2 of the receptacle and a resulting gap size fluctuation (ΔS) between the receptacle 20 and the active body. FIG. 1c shows the original diameter d1 and the changed diameter d2 of the receptacle 20 after the bulging, wherein d2−d1 corresponds to ΔS (max), that is to say the maximum size fluctuation of the gap 31 along the bulging of the receptacle 20 which the sealing lip 33 has to seal.

An adaptive sealing lip of this type has the advantage that the receptacle can be of elastic configuration without impairing the functional capability of the device. For example, as shown in FIG. 1c, the sealing lip can compensate for a partial change in the diameter on account of the bulging of up to 1 mm, for example 1.2 mm, for a receptacle with a diameter of 8 mm.

FIG. 1a shows the receptacle 20 with an opening 52, wherein the force transmission body 50 extends through the opening 52, and the sealing lip 33 is arranged at an end 22 of the active body 35, which end 22 faces the opening 52 of the receptacle 20. The force transmission body 50 can be displaced along a pull-out direction B. The pull-out direction B runs substantially along the longitudinal axis of the active body 1. As shown in detail in FIG. 1b and FIG. 1c by way of example, the sealing lip 33 extends in the direction of the opening 52 of the receptacle 20 beyond the active body 35, in order to form a projection in a pull-out direction of the active body 35.

This has the advantage that the sealing lip has a damping action when the active body comes into contact with the second end. This is the case, for example, when the device is activated at physiological speeds (see FIG. 5). Damage of the active body as a result of the impact on the receptacle can be avoided by way of the damping action of the sealing lip.

Figure 1D:
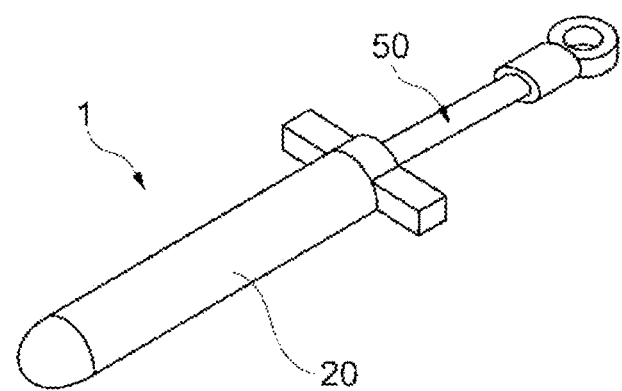

FIG. 1d shows a perspective view of the device 1. The force transmission body 50 protrudes out of the receptacle 20. Here, the receptacle 20 can be fastened to a body location of a user or sports device such as a sports shoe, for example. That end of the force transmission body 50 which lies outside the device 20 can be fastened to a second body location. The receptacle 20 is of cylindrical configuration. As an alternative, the receptacle can also be of cuboid or oval configuration.

Figure 2:
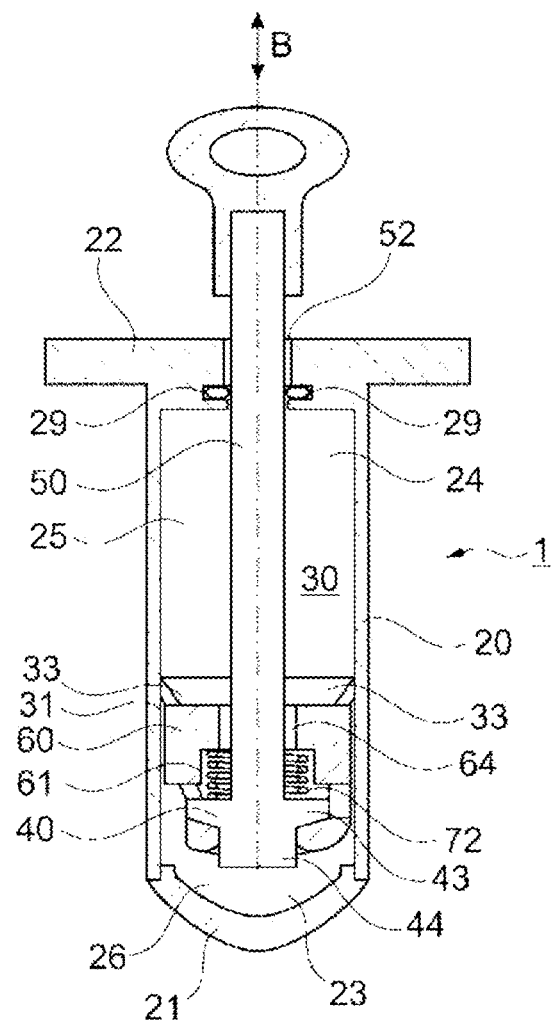

FIG. 2 shows a further embodiment of the device 1. Here, the active body arrangement has a first active body 40 and a second active body 60, the first active body 40 and the second active body 60 being arranged displaceably in the receptacle 20, and it being possible for them to interact with the filling medium 30, a force transmission body 50 transmitting the external force to the first active body 40, the second active body 60 being coupled elastically to the first active body 40 via a coupling element 72, the second active body 60 and/or the first active body 40 having at least one passage opening 64, through which the filling medium 30 can flow. The passage opening 64 in the second active body 60 provides a hydraulic diameter for the filling medium, through which hydraulic diameter the filling medium 30 can flow as long as there is a spacing between the first active body 40 and the second active body 60.

Moreover, the first active body 40 forms a valve body, and the second active body 60 forms a valve seat, the sealing lip 33 being arranged on the second active body 60. As a result, a flow of the medium through the passage opening 64 can be permitted or prevented in a manner which is dependent on the valve position. Through the passage opening 64, the flow of the filling medium can be permitted or prevented in a manner which is dependent on the valve position. External forces which act on the first active body 40 can be transmitted via the coupling element 72 to the second active body 60. Accordingly, the first active body 40 is capable of pushing and/or pulling the second active body 60 through the filling medium by means of the coupling element 72. The second active body 60 is arranged closer to the second end 22 of the receptacle 20 in relation to the longitudinal axis of the receptacle, the first active body 40 being arranged closer to the first end 21 in relation to the longitudinal axis.

The second active body 60 has a receiving space 61 which extends toward the first active body 40 and overlaps with the latter. The receiving space 61 is configured to engage behind the first active body 40. Here, the first active body 40 is received partially in the receiving space 61.

In accordance with the present embodiment, the first active body 40 is of step-shaped configuration. The first active body 40 thus has a first section 43 which is received displaceably in the receiving space 61 of the second active body 60, and a second section 44 which is tapered in terms of diameter with respect to the first section 43 and extends out of the receiving space in the direction of the movement direction B. The receiving space 61 is configured in such a way that it engages behind the first section 43 of the first active body 40 and forms a guide in the movement direction B for the second section 44. In this way, the first active body 40 can be centered with respect to the second active body 60, with the result that closure of the passage opening 64 can always be ensured when the first active body 40 and the second body 60 assume a closed valve position.

Here, the coupling element 72 is configured in such a way that, in the case of the action of an external force on the first active body, in the range of a physiological speed, it transmits a force to the second active body 60, with the result that the latter can be moved together with the first active body 40 through the filling medium.

If the force which acts via the first active body 40 and the coupling element 72 on the second active body leads to critical relative displacement speeds in the device, that is to say to non-physiological speeds, the coupling element 72 yields, as a result of which the first active body 40 moves toward the second active body 60. As a result, the hydraulic diameter decreases until the valve which is formed by way of the two active bodies is closed.

If there is no longer a hydraulic diameter available, through which the filling medium can flow, the first active body 40 and the second active body 60 cannot be moved further through the filling medium. The device 1 blocks.

The sealing lip 33 therefore prevents it from being possible for the filling medium to flow via the gap 31, and ensures this even in the case of bulging of the receptacle 20 by way of the adaptive configuration of the sealing lip (see FIG. 1*c*).

The second active body 60 can be deformed by way of the impact of the first active body 40 on the active body 60. Up to 1000 bar pressure can act partially on the second active body at the contact location of the first active body 40 with the second active body 60. Therefore, in a further embodiment, the second active body 60 can have an advantageous component design which can be realized in the form of a corresponding material pairing (hard component/soft component) via a two-component injection molding operation. Here, that region of the second active body which comes into contact with the first active body can be molded from a material with a high strength (for example, modulus of elasticity 1800 MPa), the opposite side of the second active body, that is to say the side which configures the sealing lip, being molded from a soft component with a high elasticity (for example, modulus of elasticity 300-700 MPa).

As an alternative, an insert/liner component (not shown) made from a hard component such as metal can also be arranged in the receiving space 61.

The corresponding advantageous design and/or the metal insert can prevent the first active body 40 or the first section 43 from pressing or acting on the second active body 60 in a destructive manner.

Figure 3A:
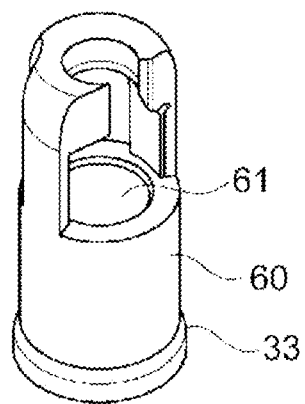
FIG. 3a shows a perspective view of the second active body of the device from FIG. 2, FIGS. 3b and 3c schematically shows side views of the second active body of the device from FIG. 2, FIGS. 4a-4g show perspective views and schematic sectional views of various embodiments of the sealing lip, FIG. 5 schematically shows a sectional view of a device for stabilizing movements of two parts, movable relative to one another, of a body region and/or a sports device with an end stop, and FIG. 6 schematically shows a sectional view of a device for stabilizing movements of two parts, movable relative to one another, of a body region and/or a sports device in accordance with a further embodiment.
Figure 3B:
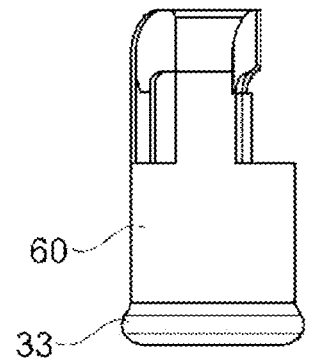
Figure 3C:
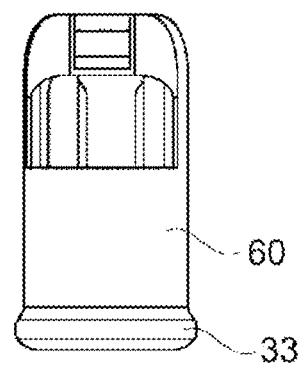

FIG. 3*a*-FIG. 3*c* show diagrammatic views of the second active body 60. The second active body 60 is designed in such a way that the coupling transmission body, the coupling element and the first active body are enclosed therein. The second active body 60 has a cage-like receiving space (see also FIG. 2).

Together with the active body 60, the sealing lip 33 forms an active body arrangement. In accordance with the embodiment which is shown here, the sealing lip 33 can be spread in a parasol-like manner by the second active body 60 in order to close the gap between the second active body 60 and the receptacle. As a result, a fully circumferential seal of the gap 31 can be ensured.

The sealing lip which is spread apart by the active body 40 is arranged at an angle α, β between the longitudinal axis and a perpendicular of the longitudinal axis in space, that is to say in the angular range of greater than 0° and less than 90°, for example greater than 10° and less than 80° in relation to the longitudinal axis of the active body. 0° is to be understood to be an orientation of the sealing lip which would run parallel to the longitudinal axis of the active body. 90° is to be understood to be an orientation of the sealing lip which would run perpendicularly with respect to the longitudinal axis of the active body.

FIG. 4*a* to FIG. 4*f* show further alternative embodiments of the sealing lip. As shown here, the sealing lip 33 which projects from the active body can be configured in various forms. For example, the sealing lip can be of rectilinear (see FIG. 4*a* or FIG. 4*b*) or curved (see FIG. 4*c*) configuration. As shown here, the sealing lip 33 can be made in different ways in the active body 35, 60. In one example, the sealing lip 33 is molded onto the active body 35, 60 by means of a two-component injection molding method, at least the sealing lip comprising a polymer, in particular from the class of polyhalogenolefins, such as polytetrafluoroethylene (PTFE).

Figure 4E:
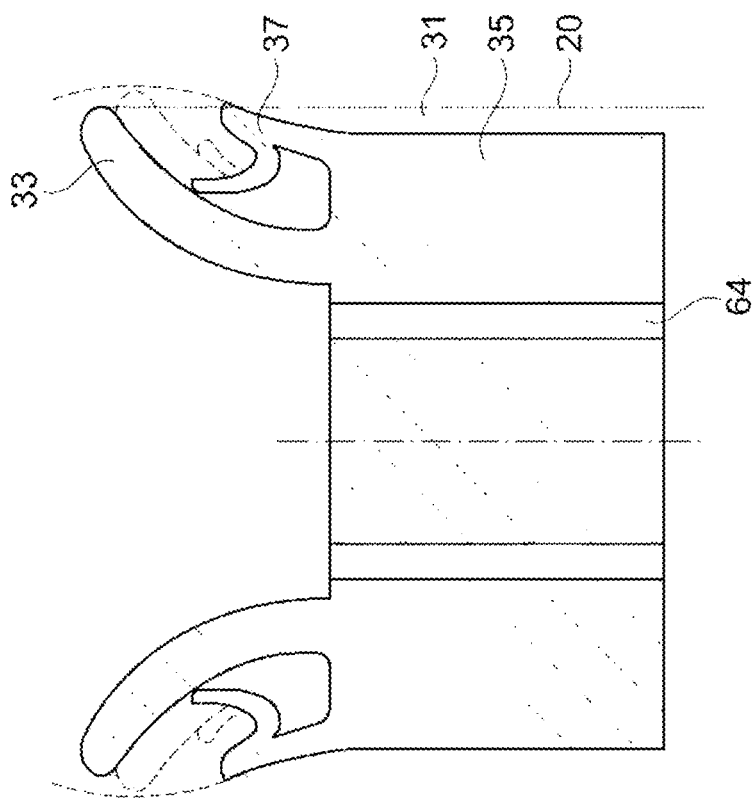
Figure 4D:
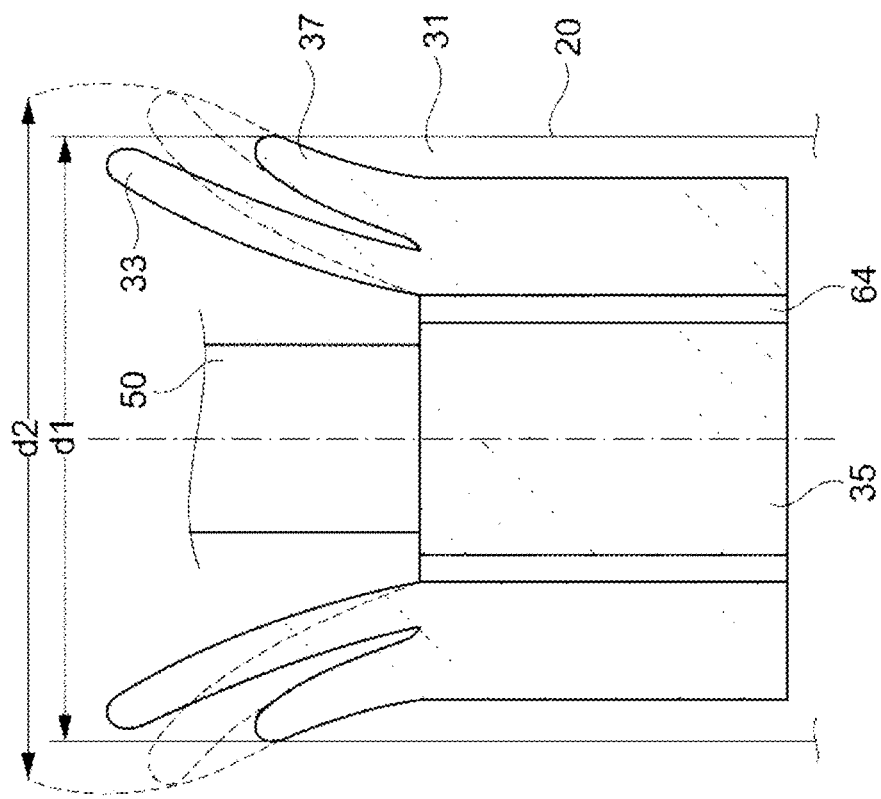

Furthermore, as shown in FIG. 4*d*, the sealing lip 33 can be limited in terms of its movement by way of a limiting element 37. As a result, a small gap can always be provided between the sealing lip 33 and the receptacle 20. In one example, the limiting element 37 can be dimensioned in such a way (for example, a hard plastic with a higher modulus of elasticity than the sealing lip) that widening of the sealing lip in the direction of the inner wall of the receptacle is prevented above a certain pressure in the receptacle. In the starting state, the sealing lip does not bear against the limiting element 37. In the spread state, characterized by the dashed line, the sealing lip spreads out in the direction of the inner wall of the receptacle 20; but only as far as the limiting element 37 allows it. As a result, it can be ensured that a small film of filling medium can flow through the gap, as a result of which critical, high pressures can be avoided. At the same time, the provided gap is set by way of the limiting element in such a way that no pressure loss arises and the device still blocks.

FIG. 4*e* shows a further embodiment of a limiting element 37. As shown, the limiting element can additionally have elastic properties which can restore the sealing lip 33 into the starting state (see dashed illustration). Here, the restoring element can act resiliently, for example, with the result that the sealing lip is restored immediately after loading. At the same time, the limiting element 37 is configured in such a way that the sealing lip 33 can be limited in terms of the widening. It is the case here, as described above, that the sealing lip can spread out up to a certain pressure. As soon as a critical pressure is reached in the receptacle 20, the limiting element 37 limits further widening and therefore ensures that excessively high pressures do not arise in the receptacle 20.

Figure 4F:
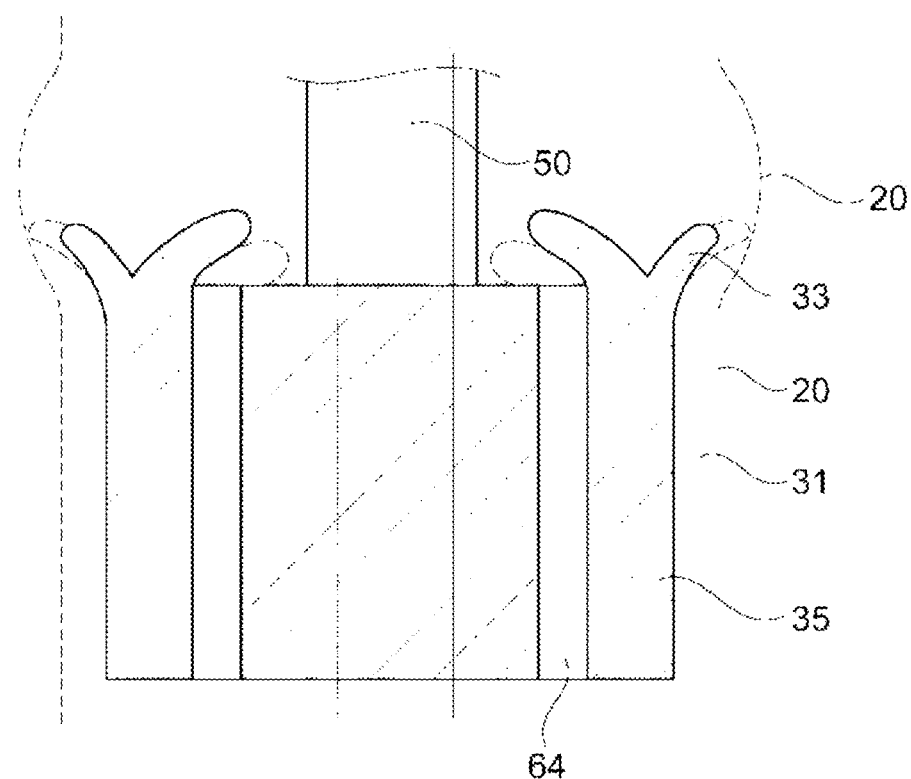

FIG. 4*f* shows a further embodiment of the sealing lip 33. In a further embodiment, the sealing lip 33 can also be configured in such a way that it is (also) pronounced in the direction of the passage opening 64. As a result, the active body 35 can be configured in such a way that the sealing lip 33 can open and close the passage opening 64 in the active body 35 in the manner of a valve. The opening can be released again by way of the restoring properties of the sealing lip or via an additional restoring element. Here, the sealing lip 33 is configured in such a way that, in addition to the gap 31, the sealing lip 33 can also seal the passage opening 64, that is to say the flow of filling medium through the passage opening 64 can be substantially prevented. The dashed lines show the widening of the sealing lip 33, for a curved state of the receptacle. The blocking of the device can be improved by way of the additional sealing of the passage opening 64.

Figure 4G:
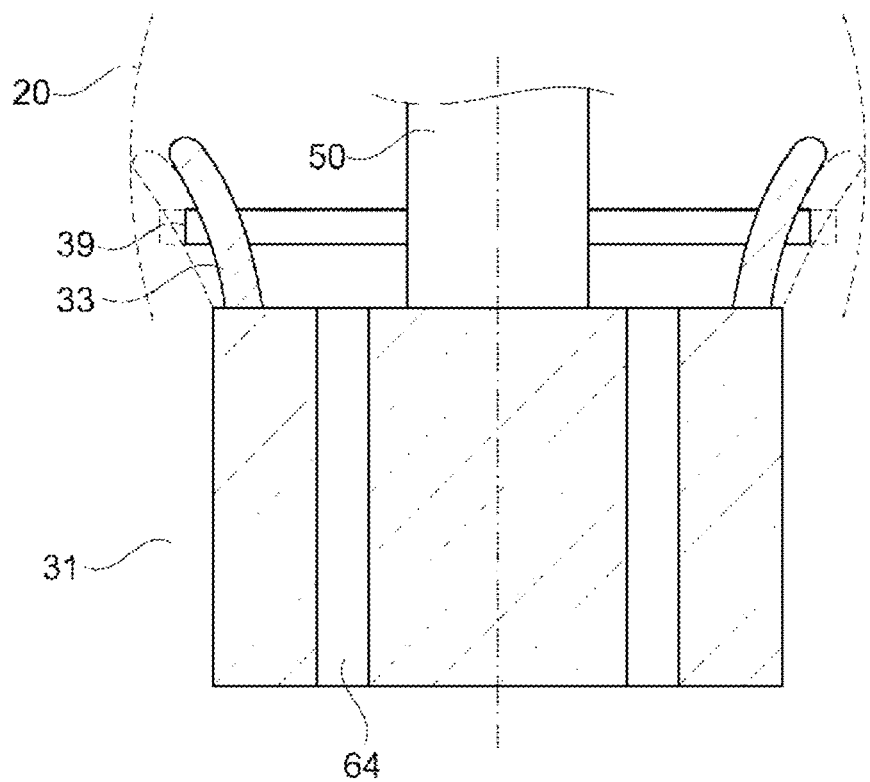

FIG. 4*g* shows a further embodiment, for limiting the widening of the sealing lip 33. Here, the active body 35 is provided via an element 39 which runs around the active body, such as a ring or a cuff, for example, with the result that the travel or the deformation range of the sealing lip is limited.

The cuff 39 is attached around the sealing lip 33. The form of the cuff 39 allows widening of the sealing lip 33 only as far as a preset point. For example, the cuff can be designed in such a way that the cuff 39 permits widening of the sealing lip (see dashed line) up to a predefined pressure (for example, 160 bar).

Figure 5:
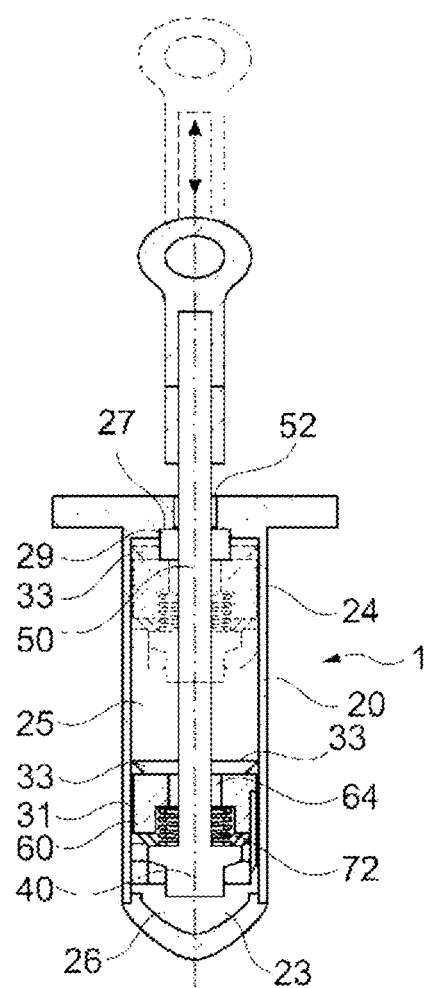

FIG. 5 shows the device 1 from FIG. 2 with an end stop 27. The end stop 27 is arranged in the region of an opening 52 of the receptacle 20, in order to avoid direct impact of the active body 60 on the receptacle. This is the case when the device is moved in the range of physiological speeds, for example if a user of the device deliberately bends over at a slow speed to such an extent that the maximum mobility of the device is exhausted. The end stop 27 can avoid the active body 60 coming directly into contact with the second end 22 of the receptacle 20. An impact of the active body on the second end 22 of the receptacle 20 can therefore be damped by means of the end stop 27.

According to FIG. 5, the end stop 27 is a damping, soft plastic which is arranged as a buffer element on the inner side of the receptacle, around the opening 52 of the receptacle 20. The buffer element can be, for example, a cushion made from a polymer, in particular from the class of polyhalogenolefins, such as polytetrafluoroethylene (PTFE).

As an alternative, an upper region of the active body which faces the second end of the receptacle might be provided with a damping, soft plastic. For example, the active body can be produced by means of a two-component injection molding method, the sealing lip 33 and the upper region consisting of a soft damping material, and the remaining region of the active body consisting of a hard material.

In a further example, the sealing lip 33 and the end stop 27 can in combination provide optimum damping of the active body.

In a further embodiment, the sealing lip 33 can also be configured in such a way that it is arranged offset with respect to the end stop of the active body. As a result, wear or even destruction of the sealing lip can be prevented in the case of repeated impact on the receptacle. Here, a section of the active body first of all makes contact with the receptacle or the end stop before the sealing lip comes into contact with the receptacle.

Figure 6:
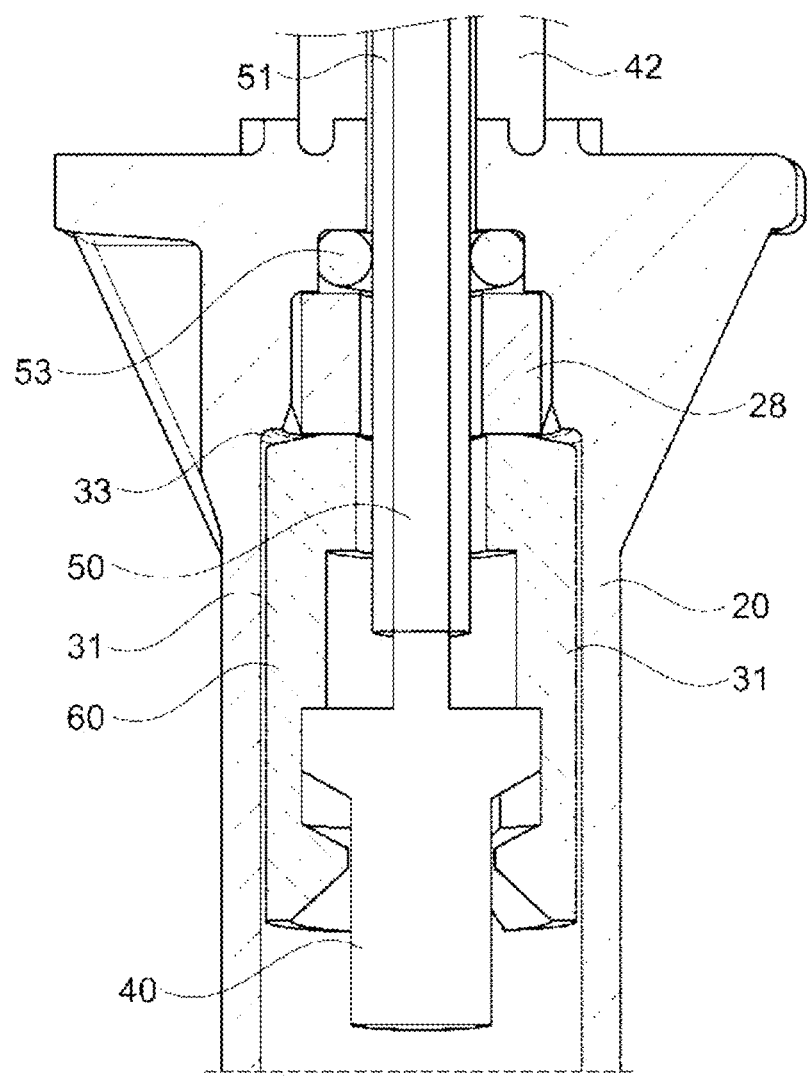

FIG. 6 shows a sectional view of a device for stabilizing body joints and/or sports devices in accordance with a further embodiment with a sealing insert 28, arranged at the opening, and a covering 51 of the force transmission body 50.

The sealing insert 28 is arranged at the opening of the device 1 below an O-ring 53 which seals the opening. The sealing insert 28 is adapted to the dimension of the receptacle 20 at the upper end of the receptacle 20 in such a way that there is a firm seat of the sealing insert 28 on the receptacle 20 by way of a non-positive connection, in particular a press fit connection between the sealing insert 28 and the receptacle 20. In one example, the active body 60 can be used to press the sealing insert 28 into the receptacle 20. As an alternative, the sealing insert 28 can be attached to the receptacle 20 by way of a positively locking or integrally joined connection. For example, the sealing insert can also be molded directly onto the receptacle in a two-component injection molding production process during the manufacture of this receptacle, and can therefore be produced in one piece with the receptacle. The seal 53 at the opening can be improved by way of the sealing insert 28, since, in addition to the sealing action of the sealing insert 28, the sealing insert 28 likewise ensures the firm seat of the O-ring 53. As a result, slipping of the O-ring 53 is avoided. At the same time, the impact protection for the active body and the sealing lip is improved.

In accordance with a further embodiment, the sealing insert 28 can be arranged on the receptacle 20 in addition to the above-described end stop.

Furthermore, in the example which is shown in FIG. 6, the force transmission body 50 is configured as a cable, in particular a wire cable (for example, a Bowden cable) which is covered by way of a cover 51 at least for the region which is in contact with the filling medium. The cover 51 has the effect of preventing filling medium from flowing into the braids of the wire cable, as a result of which a rise in the fluidic resistance (for example, turbulences which occur) as a result of the movement of the wire cable in the filling medium can be prevented. As a result, the sliding property of the force transmission body 50 in the fluid medium can be improved.

If applicable, all individual features which are shown in the individual exemplary embodiments can be combined with one another and/or swapped for one another, without departing from the scope of the invention.

LIST OF DESIGNATIONS

1 Device
20 Receptacle
21 First end
22 Second end
23 First chamber
24 Second chamber
25 Interior space of the receptacle
26 Closure
27 End stop
28 Sealing insert
29 Sealing body
30 Filling medium
31 Gap
33 Sealing lip
35 Active body
37 Limiting element
39 Cuff
40 First active body
42 Restoring element
43 First section of the first active body
44 Second section of the second active body
50 Force transmission body
51 Covering
52 Opening
53 O-ring
60 Second active body
61 Receiving space of the second active body
64 Passage opening
70 First attachment element
72 Coupling element
80 Second attachment element
S Flow direction
B Pull-out direction

The invention claimed is:

1. A device for stabilizing movements of two parts, movable relative to one another, of a body region and/or a sports device, comprising:
   a receptacle adapted to be fixed on a first part of a body region or a sports device, or both, the receptacle being filled with a filling medium,
   at least one active body arrangement with an active body which is received displaceably in the receptacle and can interact with the filling medium,
   a force transmission body which can be fixed on a second part of the same body region and/or the same sports device for transmitting an external force to the active body,
   the active body comprising at least one passage opening, through which the filling medium can flow,
   the active body arrangement comprising a sealing lip for sealing a gap between an inner side of the receptacle and a lateral region of an outer side of the active body arrangement, the sealing lip being arranged on an outer side of the active body, and
   the active body arrangement having a region of the sealing lip, which region bears against the inner side of the receptacle and extends at an angle with respect to a lateral region of the outer side of the active body, the angle being variable, the active body arrangement is configured to compensate for size fluctuations of the gap between the inner side of the receptacle and the lateral region of the outer side of the active body arrangement and configured to seal the gap even in the case of size fluctuations of this type.

2. The device as claimed in claim 1, wherein the active body arrangement is configured for the variable angle to compensate for a size fluctuation of the gap of up to 15%, in relation to the original size of the gap.

3. A device for stabilizing movements of two parts, movable relative to one another, of a body region and/or a sports device, comprising:
   a receptacle which can be fixed on a first part of a body region or a sports device, or both, the receptacle being filled with a filling medium,
   at least one active body arrangement with an active body which is received displaceably in the receptacle and can interact with the filling medium,
   a force transmission body which can be fixed on a second part of the same body region and/or the same sports device for transmitting an external force to the active body,
   the active body comprising at least one passage opening, through which the filling medium can flow,
   the active body arrangement comprising a sealing lip for sealing a gap between an inner side of the receptacle and a lateral region of an outer side of the active body arrangement, the sealing lip being arranged on an outer side of the active body
   the device being configured to allow the filling medium to flow through the gap above a size of the gap which is increased by more than 15%, in relation to the original size of the gap, to avoid a critical internal pressure in the receptacle.

4. The device of claim 1, further comprising: the sealing lip and the active body being formed in one piece.

5. The device of claim 1, wherein the receptacle comprises an opening, the force transmission body extends through the opening, and the sealing lip is arranged at an end of the active body, the end facing the opening of the receptacle.

6. The device of claim 1, the sealing lip extending at least partially in the direction of the opening of the receptacle beyond the active body, form a projection in a pull-out direction of the active body.

7. The device of claim 1, the sealing lip being configured to be spread in a parasol-like manner from the active body for closing the gap between the active body arrangement and the receptacle.

8. The device of claim 1, the sealing lip having a modulus of elasticity in the range from 300 to 700 MPa.

9. The device of claim 1, further comprising: the sealing lip being configured to permit a flow of filling medium through the gap above a determined threshold value of a force which acts on the force transmission body and a resulting determined pressure in the receptacle, to avoid a critical internal pressure in the receptacle.

10. The device of claim 1, further comprising: an end stop being arranged on the receptacle around an opening of the receptacle, and configured to prevent direct impact of the active body on the receptacle.

11. The device of claim 1, the active body comprising:
    a first active body and a second active body, the first active body and the second active body being arranged displaceably in the receptacle and the first active body and the second active body being configured to interact with the filling medium;
    the force transmission body configured to transmit the external force to the first active body;
    the second active body being coupled elastically to the first active body via a coupling element,
    the second active body, or the first active body, or both having at least one passage opening, through which the filling medium can flow, and
    the first active body forming a valve body and the second active body forming a valve seat, the sealing lip being arranged on the second active body.

12. The device of claim 1, further comprising:
    the sealing lip being molded onto the active body by way of a two-component injection molding, the sealing lip comprising a polymer.

13. The device of claim 9 wherein the sealing lip is configured to permit the flow of filling medium through the gap above the determined threshold value of a force which acts on the force transmission body and results in the determined pressure in a first chamber of the receptacle.

14. A device for stabilizing movements of two parts, movable relative to one another, of a body region and/or a sports device, comprising:
    a receptacle adapted to be fixed on a first part of a body region or a sports device, or both, the receptacle being filled with a filling medium,
    at least one active body arrangement with an active body which is received displaceably in the receptacle and can interact with the filling medium,
    a force transmission body which can be fixed on a second part of the same body region and/or the same sports device for transmitting an external force to the active body,
    the active body comprising at least one passage opening, through which the filling medium can flow,
    the active body arrangement comprising a sealing lip for sealing a gap between an inner side of the receptacle and a lateral region of an outer side of the active body arrangement, the sealing lip being arranged on an outer side of the active body, and the sealing lip and the active body being formed in one piece.

* * * * *